United States Patent [19]

Vogt et al.

[11] 4,146,503

[45] Mar. 27, 1979

[54] PROCESS FOR PREPARING A CATALYST FOR REDUCING CARBON MONOXIDE

[75] Inventors: Wilhelm Vogt, Hürth; Jürgen Koch, Brühl; Hermann Glaser, Erftstadt, all of Fed. Rep. of Germany

[73] Assignee: Hoechst Aktiengesellschaft, Frankfurt am Main, Fed. Rep. of Germany

[21] Appl. No.: 854,147

[22] Filed: Nov. 23, 1977

[30] Foreign Application Priority Data

Nov. 27, 1976 [DE] Fed. Rep. of Germany ....... 2653986
Feb. 4, 1977 [DE] Fed. Rep. of Germany ....... 2704575

[51] Int. Cl.² .................... B01J 21/12; B01J 23/72; B01J 23/74
[52] U.S. Cl. ................... 252/455 R; 252/472; 252/474; 260/449.6 R; 260/449.6 M
[58] Field of Search ............. 252/455 R, 474, 472; 260/449 R, 449.6 R, 449.6 M

[56] References Cited

U.S. PATENT DOCUMENTS

| 2,234,246 | 3/1941 | Groombridge et al. | 260/449.6 |
|---|---|---|---|
| 2,753,367 | 7/1956 | Rottig et al. | 252/474 X |
| 2,767,202 | 10/1956 | Rottig | 260/449.6 |

*Primary Examiner*—W. J. Shine
*Attorney, Agent, or Firm*—Connolly and Hutz

[57] ABSTRACT

A catalyst containing iron or a mixture of iron with copper as its active ingredient, made by precipitating a complex salt of the general formula:

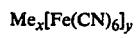

$$Me_x[Fe(CN)_6]_y$$

in which Me stands for an iron and/or copper ion, X stands for 1, 2, 3 or 4, and y stands for 1, 2 or 3; separating and drying the precipitated salt, and reducing the salt by contacting it with at least stoichiometric proportions of hydrogen or a mixture of hydrogen and carbon monoxide, for use in the reduction of carbon monoxide by means of hydrogen with the resultant formation of a mixture consisting substantially of $C_1$-$C_4$ hydrocarbons is modified. The modified catalyst is formed (a) by subjecting the precipitated and dried salt to thermal decomposition at a temperature of 200 to 500° C in the absence of hydrogen or a mixture of hydrogen and carbon monoxide, or (b) mixing the precipitated and dry salt with a carrier, tabletting, pelletizing or extruding the resulting mixture and reducing it by means of hydrogen or a mixture of hydrogen and carbon monoxide, or (c) mixing the precipitated and dry salt with a carrier, tabletting, pelletizing or extruding the resulting mixture and thermally decomposing it at 200 to 500° C in the absence of hydrogen or a mixture of hydrogen and carbon monoxide.

4 Claims, No Drawings

PROCESS FOR PREPARING A CATALYST FOR REDUCING CARBON MONOXIDE

This invention relates to a catalyst for reducing carbon monoxide and is an improvement in, or modification of, the catalyst disclosed in Patent Application Ser. No. 732,017, filed Oct. 13, 1976, now abandoned.

Patent Application Ser. No. 732,017 relates to a catalyst for reducing carbon monoxide by means of hydrogen with the resultant formation of a mixture consisting substantially of $C_1$-$C_4$ hydrocarbons, the catalyst, which contains iron or a mixture of iron with copper as its active ingredient, being made by precipitating a complex salt of the general formula:

$$Me_x[Fe(CN)_6]_y$$

in which Me stands for an iron and/or copper ion, x stands for 1, 2, 3 or 4, and y stands for 1, 2 or 3; separating and drying the precipitated salt, and reducing the salt by contacting it over a period of 2 to 20 hours, at a temperature of 200 to 500° C. and under a pressure of 1 to 100 atmospheres absolute, with at least stoichiometric proportions of hydrogen or a mixture of hydrogen and carbon monoxide.

The catalyst described may be used in the form of granules or pellets, or may be deposited on a carrier, such as aluminum oxide, silicic acid, kieselguhr, asbestos, glass fibers, clay minerals, pumice or active carbon. In those cases in which use is made of a carrier-supported catalyst, 20 to 95 weight % of the catalytically active ingredient should preferably be applied to the carrier, the percentage being based on the total weight of catalytically active ingredient and carrier.

The catalyst described is a precipitation catalyst which means that the iron cyanides or copper cyanides are generally obtained by precipitating them from an aqueous alkali metal ferrocyanide solution with the aid of an aqueous iron and/or copper salt solution, and separating and drying the precipitated salt. The precipitation may also be effected in an inversed sequential order.

Thus, for example, it is possible to prepare the catalyst by precipitating copper ferrocyanide from an aqueous copper (II) salt solution by means of an aqueous solution of potassium ferrocyanide. The resulting redbrown precipitate is suction-filtered, washed and dried. Next, the precipitate is activated for about 2 hours at 350 to 400° C. by means of hydrogen in a copperlined steel tube.

It is also possible to produce an almost white precipitate from an ammoniacal solution of copper (I) chloride and potassium ferrocyanide, which are used in a molar ratio of 4:1. The precipitate is dried and activated by means of hydrogen, and a very good hydrogenation catalyst is obtained.

A further method for making an efficient hydrogenation catalyst comprises reacting an aqueous solution of a copper (II) salt and an iron (II) salt with potassium ferrocyanide in a molar ratio of 1:1:1, separating the resulting blue-black precipitate, drying and activating it with hydrogen. A catalyst made from a mixture of ferri/ferrocyanides also has good hydrogenating properties.

The primary catalysts prepared in the manner described hereinabove can, for example, be applied to a carrier by precipitating the complex cyanides in an aqueous suspension of the carrier, separating the resulting mixture of precipitated cyanide and carrier, drying the mixture, washing it and reducing the cyanides by means of hydrogen at the necessary temperature.

Another method of applying the catalyst to the carrier comprises impregnating preformed carrier material with the complex cyanides by first impregnating the carrier with an aqueous solution of potassium ferrocyanide, then drying the carrier so impregnated and reaching the carrier with an aqueous solution of a copper salt and/or iron salt. This sequential order of steps may be inversed, i.e. the carrier can first be impregnated with the aqueous solution of the copper salt and/or iron salt, and can then be precipitated by means of potassium ferrocyanide.

A still further method comprises mixing the aqueous solution of potassium ferrocyanide with a copper salt in the presence of ammonia (precipitation is obviated, e.g. in those cases in which a copper (II)-salt and potassium ferrocyanide are used), impregnating the carrier with the resulting solution and precipitating the copper-cyanide complex by evaporation of the ammonia.

It is not absolutely necessary for the precipitated and dry salts to be treated with hydrogen. The salts can also be contacted with a $CO/H_2$-mixture and pure CO so as to activate the cyanide complex. A catalyst so prepared was taken after about 8 hours of operation from a reactor. The complex cyanide was found to have been extensively destroyed.

In accordance with our present invention, we have now unexpectedly found that it is not obligatory (a) for the catalyst to be applied in the manner described in Patent Application Ser. No. 732,017 and (b) for the precipitated and dried iron cyanides or iron-copper cyanides to be thermally treated and activated in contact with hydrogen or a mixture of hydrogen and carbon monoxide.

The invention thus provides for the catalyst containing iron or a mixture of iron with copper as its active ingredient, made by precipitating a complex salt of the general formula:

$$Me_x[Fe(CN)_6]_y$$

in which Me stands for an iron and/or copper ion, x stands for 1, 2, 3 or 4, and y stands for 1, 2 or 3; separating and drying the precipitated salt, and reducing the salt by contacting it over a period of 2 to 20 hours, at a temperature of 200 to 500° C., with at least stoichiometric proportions of hydrogen or a mixture of hydrogen and carbon monoxide, for use in the reduction of carbon monoxide by means of hydrogen with the resultant formation of a mixture consisting substantially of $C_1$-$C_4$ hydrocarbons, to be modified, the modified catalyst being made by (a) forming it by subjecting the precipitated and dried salt to thermal decomposition at a temperature of 200 to 500° C. in the absence of hydrogen or a mixture of hydrogen and carbon monoxide, or (b) mixing the precipitated and dry salt with a carrier, tabletting, pelletizing or extruding the resulting mixture and reducing it by means of hydrogen or a mixture of hydrogen and carbon monoxide, or (c) mixing the precipitated and dry salt with a carrier, tabletting, pelletizing or extruding the resulting mixture and thermally decomposing it at 200 to 500° C. in the absence of hydrogen or a mixture of hydrogen and carbon monoxide.

A preferred feature of the present process for making the catalyst comprises thermally decomposing the dried salt under vacuum, e.g. under a pressure of about 1 to less than 760 mm Hg, or under a pressure of 1 to 100 atmospheres absolute.

The preferred carrier is alumino-silicate, but aluminum oxide, silicic acid, kieselguhr, asbestos, glass fibers, clay minerals, pumice or active carbon can also be used.

As more fully illustrated in the following Examples, the present catalyst compares favorably with the prior art catalysts in respect of the following points: It can be made under commercially attractive conditions and combines this with a relatively high selectivity in the reaction of carbon monoxide with hydrogen with the resultant formation of $C_1$-$C_4$ hydrocarbon mixtures.

EXAMPLE 1

(a) Catalyst Preparation 165 g of $CuSO_4 \cdot 5 H_2O$ and 185.6 g of $FeSO_4 \cdot 7 H_2O$ were dissolved in 1 liter of $H_2O$ and the solution was heated to 40° C. Next, it was added within 30 minutes to a solution of 253 g of $K_4[Fe(CN)_6]$ in 2 liters of water, which had a temperature of 60° C. After the precipitation was complete, the precipitate was allowed to remain for 2 hours at 60° C in the mother liquor, then filtered off while hot and washed twice, each time with 2 liter of $H_2O$. The filter cake was dried at 60° C. 40 g of the primary product so obtained was thoroughly mixed with 40 g of an alumino-silicate containing about 70% of $SiO_2$ and 15% of $Al_2O_3$ (TONSIL L 80, this is a registered Trade Mark in the name of Sudchemie AG, Munchen) and 4 g of pulverulent graphite, and the resulting mixture was compressed into tablets 2.4 mm in diameter. The tabletted material had a bulk density of 77 g/100 ml. and was composed of: 10.5 weight % of $H_2O$, 9.7 weight % of N, 4.6 weight % of K, 7 weight % of Cu, 10.9 weight % of Fe, the balance being carrier and carbon. 10 g of the tabletted product was pretreated over a period of 16 hours at 350° C. with hydrogen under a pressure of 10 atmospheres gauge at a space velocity of 770 liter per hour per liter of catalyst.

(b) Use of Catalyst

The catalyst pretreated in the manner described was contacted with a mixed gas consisting of 48 volume % of CO and 52 volume % of $H_2$ at a space velocity of 400 liters per hour per liter of catalyst. The reaction pressure was 20 atmospheres gauge. The issuing gas obtained at 340 to 350° C. was composed of: 28.5 volume % of CO, 4.5 volume % of $CH_4$, 20.6 volume % of $CO_2$, 0.8 volume % of $C_2H_4$, 1.2 volume % of $C_2H_6$, 1.2 volume % of $C_3H_6$, 0.25 volume % of $C_3H_8$.

EXAMPLE 2

(a) Catalyst Preparation 165 g of $CuSO_4 \cdot 5 H_2O$ and 185.6 g of $FeSO_4 \cdot 7 H_2O$ were dissolved in 1 liter of $H_2O$ and the solution was heated to 40° C. Next it was introduced within 30 minutes to a 60° C. solution of 253 g of $K_4[Fe(CN)_6]$ in 2 liters of water. After the precipitation was complete, the precipitate was allowed to remain in the mother liquor for 2 hours at 60° C., filtered off while hot and washed twice, each time with 2 liters of water. The filter cake was dried for 20 hours at 60°C., stirred once again into 1 liter of water, washed twice with 2 liters of water, and filtered off with suction. The filter cake was dried, again at 60° C. 40 g of the primary product so obtained was wetted with little water, then thoroughly kneaded with 40 g of an aluminosilicate (TONSIL L 80, this is a registered Trade Mark in the name of Sudchemie) and the whole was extruded on a 2 mm rolling extruder into articles 2 mm in diameter and 2 to 3 mm long. The articles were dried and a product with a bulk density of 79 g/100 ml was obtained. Its analytic composition corresponded to that indicated for the product of Example 1.50 ml of this catalyst was treated for 2 hours at 320° C. under a pressure of 10 atmospheres gauge with $H_2$. The space velocity was 770 l of $H_2$ per hour per liter of catalyst.

(b) Use of Catalyst

The catalyst pretreated in the manner just described was contacted with a mixed gas consisting of 50 volume % of CO and 50 volume % of $H_2$ at a space velocity of 500 l per hour per liter of catalyst. The reaction pressure was 10 atmospheres gauge. The issuing gas obtained at 340° C. was composed of: 18.2 volume % of CO, 14.0 volume % of $CH_4$, 0.7 volume % of $C_2H_4$, 3.6 volume % of $C_2H_6$, 2.76 volume % of $C_3H_6$, 1.2 volume % of $C_3H_8$, 38.0 volume % of $CO_2$.

EXAMPLE 3

(a) Catalyst Preparation 165 g of $CuSO_4 \cdot 5 H_2O$ and 185.6 g of $FeSO_4 \cdot 7 H_2O$ were dissolved in 1 liter of $H_2O$ and the solution was heated to 40° C. Next, it was introduced within 30 minutes into a solution of 253 g of $K_4[Fe(CN)_6]$ in 2 liters of water, at 60° C. After the precipitation was complete, the precipitate was allowed to remain in the mother liquor for 2 hours at 60° C, filtered off while hot and washed twice with 2 l of $H_2O$. The filter cake was dried at 60° C. 40 g of the product so obtained was thoroughly mixed with 40 g of alumino-silicate (TONSIL L 80) and 4 g of pulverulent graphite and the mixture was compressed into tablets 2 to 4 mm in diameter. The tabletted material had a bulk density of 77 g/100 ml and was composed of 10.5 weight % of $H_2O$, 9.7 weight % of N, 4.6 weight % of K, 7 weight % of Cu, 10.9 weight % of Fe, the balance being carrier and carbon. 10 g of the tabletted product was placed in a reactor and heated to 320°C., over a period of about 2 hours.

(b) Use of Catalyst

After the 320° C temperature had been reached in the reactor, the tabletted catalyst was contacted with a mixed gas composed of 48 volume % of CO and 52 volume % of $H_2$ at a space velocity of 800 liters per hour per liter of catalyst. The reaction pressure was 10 atmospheres gauge. The issuing gas obtained at 340 to 350° C. was composed of: 17.5 volume % of CO, 4.9 volume % of $CH_4$, 25.4 volume % of $CO_2$, 1.8 volume % of $C_2H_4$, 0.7 volume % of $C_2H_6$, 1.8 volume % of $C_3H_6$ and 0.2 volume % of $C_3H_8$.

EXAMPLE 4

(a) Catalyst Preparation

A 60° C. warm solution of 82.5 g of $CuSO_4 \cdot 5 H_2O$ and 92.8 g of $FeSO_4 \cdot 7 H_2O$ in 1 liter of $H_2O$, in which 264 g of pulverulent $SiO_2$ had been suspended, was introduced, with vigorous agitation, into a solution of 126.5 g of $K_4[Fe(CN)_6]$ in 500 ml of water. The resulting precipitate was allowed to remain in the mother liquor for 2 hours at 60° C., then suction-filtered and dried at 60° C. 7 g of the catalyst so obtained was mixed with 10 g of an inert carrier consisting of particles with a size of 0.5 to 0.3 mm ($Al_2O_3$, grade Condea NG, a commercially available product of Petrochemie-Gesellschaft, Hamburg), and the mixture was placed in a tubular reactor. The reactor was evacuated so as to establish a pressure of about 2 mm Hg and heated to 310° C.

(b) Use of Catalyst

The catalyst was contacted with a mixed gas composed of 50 volume % of CO and 50 volume % of $H_2$ under a pressure of 10 atmospheres gauge. The composition of the issuing gas varied in accordance with its velocity. This is shown in the following Table.

TABLE

| Temp. °C | Pressure atm.gauge | Velocity issuing gas l/h | CO | $CO_2$ | $CH_4$ | $C_2H_4$ in volume % | $C_2H_6$ | $C_3H_6$ | $C_3H_8$ |
|---|---|---|---|---|---|---|---|---|---|
| 330 | 10 | 15 | 21.6 | 22.4 | 5.3 | 1.5 | 0.5 | 1.3 | 0.1 |
| 335 | 10 | 20 | 24.3 | 21.0 | 5.4 | 1.35 | 0.6 | 1.4 | 0.2 |
| 340 | 10 | 30 | 23.7 | 21.5 | 7.5 | 1.4 | 0.9 | 1.2 | 0.2 |
| 335 | 10 | 40 | 27.3 | 19.0 | 7.1 | 1.2 | 0.9 | 1.1 | 0.2 |
| 340 | 10 | 50 | 28.8 | 18.0 | 7.0 | 1.1 | 0.85 | 1.0 | 0.2 |
| 335 | 10 | 60 | 30.0 | 16.7 | 6.3 | 1.0 | 0.7 | 0.9 | 0.1 |
| 340 | 12 | 70 | 30.3 | 16.8 | 6.4 | 1.0 | 0.8 | 0.9 | 0.2 |
| 345 | 12 | 80 | 29.7 | 17.6 | 7.2 | 1.0 | 0.9 | 0.9 | 0.3 |

We claim:
1. In the process for preparing a catalyst for the reduction of carbon monoxide by means of hydrogen with the resultant formation of a mixture consisting essentially of $C_1$-$C_4$ hydrocarbons, said catalyst containing iron or a mixture of iron and copper as its active ingredient and being made by precipitating a complex salt of the formula

$$Me_x[Fe(CN)_6]_y$$

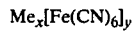

in which Me is an iron ion and/or a copper ion, x is 1, 2, 3 or 4, and y is 1, 2, or 3; separating and drying the precipitated salt, and reducing the salt by contacting it for 2–20 hours at 200–500° C. with at least stoichiometric proportions of hydrogen or a mixture of hydrogen and carbon monoxide, the improvement which comprises:
   (a) forming the catalyst by subjecting the precipitated and dried salt to thermal decomposition at 200–500° C. in the absence of hydrogen or a mixture of hydrogen and carbon monoxide, or
   (b) mixing the precipitated and dry salt with a carrier, tabletting, pelletizing or extruding the resulting mixture and reducing it by means of hydrogen or a mixture of hydrogen and carbon monoxide, or
   (c) mixing the precipitated and dry salt with a carrier, tabletting, pelletizing or extruding the resulting mixture and thermally decomposing it at 200–500° C. in the absence of hydrogen or a mixture of hydrogen and carbon monoxide.

2. The process of claim 1, wherein the salt is thermally decomposed under vacuum or under a pressure of 1–100 atmospheres absolute.

3. The process of claim 2, wherein the vacuum is about 1 to less than 760 mm Hg.

4. The process of claim 1, wherein the catalyst is deposited on alumino-silicate.

* * * * *